United States Patent [19]

Gough et al.

[11] 4,031,237

[45] June 21, 1977

[54] CARBAMATE INSECTICIDES FROM 5,8-DIHYDRO-5,8-METHANO-1-NAPHTHOL AND ITS DERIVATIVES

[75] Inventors: Stanley T. Gough, Branchburg; Michael A. Tobias, Edison; Roger P. Napier, Somerville, all of N.J.

[73] Assignee: Mobil Oil Corporation, New York, N.Y.

[22] Filed: Mar. 30, 1971

[21] Appl. No.: 129,628

Related U.S. Application Data

[63] Continuation-in-part of Ser. No. 764,969, Oct. 3, 1968, abandoned.

[52] U.S. Cl. .......................... 424/278; 260/348 C; 260/454; 260/465 B; 260/479 C; 424/300

[51] Int. Cl.² ................ C07D 303/36; A01N 9/28
[58] Field of Search .............. 260/479 C, 348 C; 424/278

*Primary Examiner*—Anton H. Sutto
*Attorney, Agent, or Firm*—Charles A. Huggett; Hastings S. Trigg

[57] ABSTRACT

N-substituted carbamates derived from 5,8-dihydro-5,8-methano-1-naphthol and substituted derivatives therefor are new compounds having insecticidal activity. These tricyclic phenols are prepared, for example, by Diels-Alder condensation of cyclopentadiene with 2-cyclohexen-1-one (or substituted derivative), followed by dehydrogenation.

6 Claims, No Drawings

CARBAMATE INSECTICIDES FROM 5,8-DIHYDRO-5,8-METHANO-1-NAPHTHOL AND ITS DERIVATIVES

CROSS-REFERENCE TO RELATED APPLICATIONS

This application is a continuation-in-part of co-pending application Ser. No. 764,969, filed Oct. 3, 1968, now abandoned.

BACKGROUND OF THE INVENTION

1. Field of the Invention

This application is directed to a new class of carbamate pesticides. It is more particularly concerned with insecticidal carbamates of tricyclic phenols.

2. Description of the Prior Art

Carbamates of various phenols have shown biological activity of varying scope and degree. Typical carbamates are those of α-naphthol and of 4-hydroxy-benzothiophene (U.S. Pat No. 3,288,673). Insofar as is now known, however, carbamates of tricyclic phenols have not been proposed.

SUMMARY OF THE INVENTION

This invention provides a novel class of carbamates having the formulae:

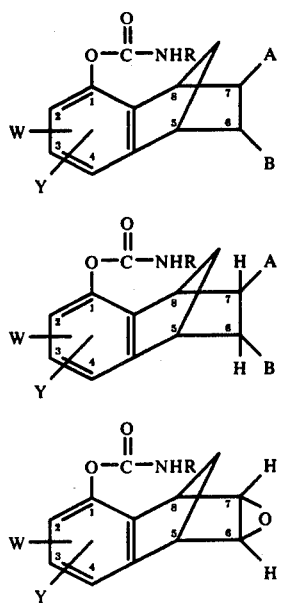

wherein A and B are selected from hydrogen, halogen (Cl or Br), cyano, thiocyanato, alkoxy ($C_1$–$C_5$) alkylthio ($C_1$–$C_5$), carbalkoxy, and alkyl ($C_1$–$C_5$); W and Y can occupy any separate 2, 3, and 4 position and are selected from hydrogen, alkyl ($C_1$–$C_5$), halogen (Cl or Br), nitro, cyano, carbalkoxy, alkoxy ($C_1$–$C_5$), alkylthio ($C_1$–$C_5$), and di-($C_1$–$C_5$) alkylamino; and R is selected from alkyl ($C_1$–$C_5$), alkenyl ($C_2$–$C_5$), phenyl, and halophenyl. It also provides the method for combatting insects that comprises contacting them with at least one of said carbamates; and insecticidal compositions comprising said carbamates and a carrier therefor.

DESCRIPTION OF SPECIFIC EMBODIMENTS

Non-limiting examples of the carbamates of this invention are: 5,8-dihydro-5,8-methano-1-naphthyl-N-methyl carbamate; 5,8-dihydro-5,8-methano-1-naphthyl-N-phenyl carbamate; 5,8-dihydro-5,8-methano-1-naphthyl-N-p-chlorophenyl carbamate; 5,8-dihydro-5,8-methano-4-methyl-1-naphthyl-N-methyl carbamate; 5,8-dihydro-5,8-methano-4-methyl-1-naphthyl-N-phenyl carbamate; 5,8-dihydro-5,8-methano-4-t-butyl-1-naphthyl-N-methyl carbamate; 5,8-dihydro-5,8-methano-4-isopropyl-1-naphthyl-N-methyl carbamate; 5,8-dihydro-5,8-methano-4-carbomethoxy-1-naphthyl-N-methyl carbamate; 5,8-dihydro-5,8-methano-4-methylthio-1-naphthyl-N-methyl carbamate; 5,8-dihydro-5,8-methano-3-methyl-4-methylthio-1-naphthyl-N-methyl carbamate; 5,8-dihydro-5,8-methano-4-dimethylamino-1-naphthyl-N-methyl carbamate; 5,8-dihydro-5,8-methano-3-methyl-4-dimethylamino-1-naphthyl-N-methyl carbamate; 5,8-dihydro-5,8-methano-2-methylthio-1-naphthyl-N-methyl carbamate; 5,8-dihydro-5,8-methano-4-chlorochloro-1-naphthyl-N-methyl carbamate; 5,8-dihydro-5,8-methano-4-nitro-1-naphthyl-N-methyl carbamate; 5,8-dihydro-5,8-methano-4-dimethylaminomethyl-1-naphthyl-N-methyl carbamate; 5,8-dihydro-5,8-methano-2-ethyl-1-naphthyl-N-methyl carbamate; 5,8-dihydro-5,8-methano-3-methyl-1-naphthyl-N-methyl carbamate; 5,6,7,8-tetrahydro-5,8-methano-1-naphthyl-N-methyl carbamate; 5,6,7,8-tetrahydro-5,8-methano-1-naphthyl-N-phenyl carbamate; 5,6,7,8-tetrahydro-5,8-methano-1-naphthyl-N-p-chlorophenyl carbamate; 5,8-dihydro-6,7-epoxy-5,8-methano-1-naphthyl-N-methyl carbamate; 5,8-dihydro-6,7-epithio-5,8-methano-1-naphthyl-N-methyl carbamate; 5,6,7,8-tetrahydro-6,7-dichloro-5,8-methano-1-naphthyl-N-methyl carbamate.

Various methods can be used to prepare the carbamates of this invention and the particular synthesis route used is not a significant factor of this invention. A particularly feasible method for preparing alkoxy-substituted derivatives is set forth in the working examples, infra, but such derivatives can be made by other methods. In general, however, the carbamates of this invention can be prepared by a three-step process. In the first step, cyclopentadiene is reacted with a 2-cyclohexen-1-one reactant by Diels-Alder condensation to produce a 1-oxo-5,8-methano-1,2,3,4,4a,5,8,8a-octahydronaphthalene. In the second step, catalytic dehydrogenation of the latter produces a 5,8-dihydro-5,8-methano-1-naphthol. Finally, in the third step, this naphthol is converted to the carbamate. Tautomerism of substituted cyclopentadiene derivatives precludes their use in synthesizing the compounds of this invention. Thus, the initial condensation reaction is carried out with cyclopentadiene itself and substituents A and B are introduced subsequently.

The 2-cyclohexen-1-one reactant is a compound having the formula:

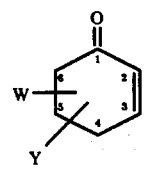

wherein W and Y can occupy any separate 4, 5, and 6 position and are selected from hydrogen, alkyl ($C_1$–$C_5$), halogen (Cl-Br), nitro, cyano, carboxy, alkoxy ($C_1$–$C_5$), alkylthio ($C_1$–$C_5$), and di-($C_1$–$C_5$) alkylamino. Substituted derivatives of 2-cyclohexen-1-one are readily prepared by well-known methods introducing substituents into a cycloalkyl ring. Typical derivatives described in the literature include 4-carbomethoxy; C.A. 46: P 10198g; 6-methylthio-, J. Chem. Soc. p. 1995 (1955); 6-ethyl-, C.A. 55: 12317a; 4-dimethylaminomethyl-, J. Chem. Soc. p. 167 (1958); 5-methyl-, J. Chem. Soc. p. 1270 (1947); and 4-isopropyl-, J. Am. Chem. Soc. 77, 1003 (1955).

The reaction of the cyclopentadiene and the 2-cyclohexen-1-one reactant is the well-known Diels-Alder condensation of an olefinic compound with a conjugated diolefinic compound. In general, the reaction will proceed at room temperature, but in some cases higher temperatures up to 190°–220°C. (and elevated pressures) will be advantageous. Preferably, an aromatic hydrocarbon solvent is used, such as benzene, toluene, and xylene. Although a catalyst is not generally necessary, a Friedel-Crafts type catalyst (e.g., aluminum chloride, aluminum bromide, zinc Chloride) can be employed. The product of this condensation is a 1-oxo-5,8-methano-1,2,3,4,4a,5,8,8a-octahydronaphthalene.

In the case wherein the desired carbamate is to be the 6,7-dihydro derivative, it is generally more feasible to saturate the double bond in the 1-oxo derivative, although the carbamate itself can be saturated. This is done by any of the well-known methods for saturating a double bond by hydrogenation, e.g., liquid phase hydrogenation in the presence of platinum or palladium metal on a charcoal support.

The 6,7-epoxy derivative can be prepared by any known means to add oxygen across a double bond. Typically, this is done by reaction of hydrogen peroxide or an organic peroxide and typical procedures are described for example, in J. Prackt. Chem. 111, 373 (1925).

In the second step, the 1-oxo derivative (saturated or unsaturated in the 6,7-position) is aromatized to a phenolic compound by dehydrogenation. This dehydrogenation can be carried out by any of the liquid phase and vapor phase processes known in the art. As illustrated in the specific working examples, the dehydrogenation can be carried out in the vapor phase in the presence of hydrogen and a supported noble metal catalyst or in the liquid phase using sulfur as hydrogen acceptor.

It is generally preferred to introduce substituents into the phenol before forming the carbamate, although some substitution can be effected in the carbamate. Typical well-known techniques that can be employed include nitration (and reduction to amino), sulfonation, chlorination and bromination, and reaction (acid) with dimethylsulfoxide to introduce methylthio.

The final step, the preparation of the carbamate, can be carried out by several well-known methods for converting phenolic compounds to carbamates. One method, as illustrated in the specific working examples, involves the reaction of the phenol with an isocyanate in the presence of a catalyst, such as dibutyltin diacetate. Another method involves forming the chloroformate intermediate (by reaction of the phenolic compound with phosgene) and then reacting it with the appropriate amine (alkylamine, aniline, dimethylaniline, substituted aniline, etc.). The method is illustrated, for example, in U.S. Pat. No. 3,288,673.

INSECTICIDE TESTING METHODS
DIP TEST

Mexican Bean Beatle — Epilachna varivestis Mulsant

Lima bean leaves of uniform size are momentarily dipped in a 500 p.p.m. water-acetone solution of the test compound. When dry, the treated leaf is placed in a screened petri dish and exposed to 10 fourth instar larvae. The percent mortality is recorded after 48 hours. Compounds that show 90 percent or more mortality are retested at 100 and 10 p.p.m.

Southern Armyworm — Prodenia eridania Cramer

The test is carried out as described for the Mexican Bean Beatle, using 10 fourth instar larvae and observing mortality after 48 hours.

Two-Spotted Spider Mite — Tetranychus telarius Linnaeus

Infested trifoliate bean leaves (Henderson bush lima) are selected that have as many as 20 adult mites per leaf. Leaves with mites attached are momentarily dipped into a 500 p.p.m. emulsion, solution, or suspension of the test compound and then placed (petiole only) in a 4 oz. bottle of water for observation. Percent mortality is observed after 72 hours. If 90–100 percent mortality is observed, compounds are retested at 100 and 10 p.p.m.

SPRAY TESTS

Housefly — Musca domestica Linnaeus

Adult houseflies are contained in 100 mm. petri dish screened cages and exposed to a spray of 10 ml. acetone solution of test compound. An initial concentration of 500 p.p.m. is used, with 10 flies in each cage. percent mortality is observed after 24 hours. When over 90 percent mortality is observed, the compound is retested at lower concentrations.

Bean Aphid — Aphis fabae

This test is conducted in a manner similar to that used for the housefly. The test specimens are Nasturtium leaves infested with bean aphids.

Boll Weevil — Anthonomus Grandis

This test is conducted in a manner similar to that used for the housefly. The test specimens are 10 boll weevils per screened petri dish.

Mosquito Larvae — Aedes aegypti Linnaeus

Early fourth stage larvae are exposed in solutions, emulsions, or suspensions of the test compound in water. The compounds are dissolved in acetone and added to jars of distilled water containing the larvae. Water-soluble compounds remain in solutions and the others form finely divided suspensions. Compounds are initially tested at 1 p.p.m. using 10 larvae per 100 ml. water. Percent mortality is observed after 24 hours. If 90–100 percent mortality occurs, compounds are retested at 0.1 and 0.01 p.p.m. Results are reported: p.p.m. conc./% kill.

EXAMPLE 1

Preparation of 1-oxo-5,8-methano-1,2,3,4,4a,5,8,8a-octahydronaphthalene

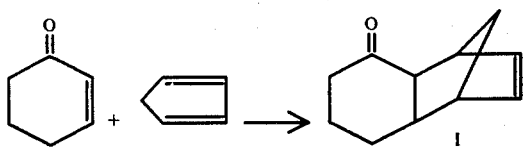

Freshly prepared cyclopentadiene (65.8g.) was dissolved in dry benzene (2820 ml.), and anhydrous zinc chloride (127.8g.) added. The mixture was stirred at room temperature and 2-cyclohexen-1-one (94.0g.) added. Stirring was continuous for 3 days, then the mixture was filtered, the filtrate washed twice with water and the solvent dried and evaporated to give the Diels-Alder adduct, I, (67.0g.). This compound could be purified by distillation, b.p. 90°– 91°/2.0mm., and its structure was confirmed by the infrared spectrum (C=O at 5.85$\mu$). It was shown to be pure by a v.p.c. analysis (2 ft. silicone gum rubber column, programmed 10°/min. from 100° C., helium flow rate 1 ml./sec.) which showed a single peak for the adduct, with a retention time of 5.3 min.

EXAMPLE 2

Preparation of 5,8-dihydro-5,8-methano-1-naphthol

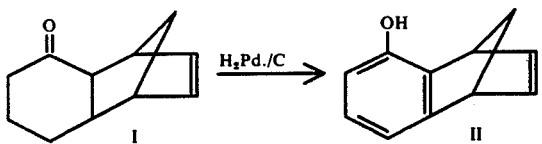

Ketone I, was aromatized to phenol II by a vapor-phase method, using the following conditions:

| | |
|---|---|
| Hydrogen gas Flow | 7 liter/hour |
| Temperature | 278–285° C. |
| Feed Rate | 15 ml./hr. of a 25% solution in I in benzene. |
| Catalyst | 5% palladium on charcoal, supported on the vapor phase apparatus on alundum. |

A 25 percent solution of I (20 ml.) was passed through the column under the above conditions, and the condensate from the column was evaporated to give an oil (3.2g.). This material was dissolved in benzene (100 ml.), and extracted with 5 percent sodium hydroxide solution (2 × 35 ml.). The caustic wash was then acidified with 10 percent hydrochloric acid solution (30 ml.), and extracted with benzene (2 × 50 ml.). The extracts were dried and the solvent removed to give the phenol, II. (1.2g.). The structure of II was indicated by its solubility in base, and confirmed by its infrared spectrum (OH absorption at 2.9$\mu$no C=O absorption), and the sample was shown to be pure by a v.p.c. analysis (using conditions as in Example I), which showed a single peak for the compound, with a retention time of 3.2 min.

EXAMPLE 3

Preparation of 1-oxo-5,8-methano-1,2,3,4,4a,5,6,7,8,8a-decahydronaphthalene.

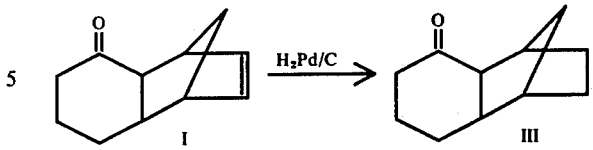

I (8.1 g.) was dissolved in methanol (50 ml.), and 5 percent palladium on charcoal (500 mg.) added. The solution was then contacted with hydrogen at atmospheric pressure in a Paar bomb. After the calculated quantity of hydrogen was absorbed, the catalyst was filtered, and the solvent removed by evaporation to give an almost quantitative yield of III, b.p. 130°–134°/16 mm.

EXAMPLE 4

Preparation of 5,6,7,8,-tetrahydro-5,8-methano-1naphthol.

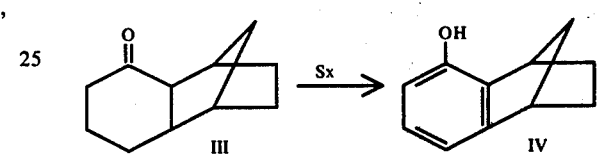

A mixture of ketone III (6.6 g.), sulfur (2.6 g.) and diphenyl ether (60 ml.) were heated at 245°–255° C. for 2½ hours. The reaction mixture was cooled, diluted with ether and extracted with dilute sodium hydroxide solution. The basic extracts were acidified and extracted with ether, and the ether extracts dried and the solvent evaporated to give the phenol IV, b.p. 121°–123°/4.5 mm. (1.3 g.).

EXAMPLE 5

Preparation of 5,8-dihydro-5,8-methano-1naphthyl-N-methylcarbamate.

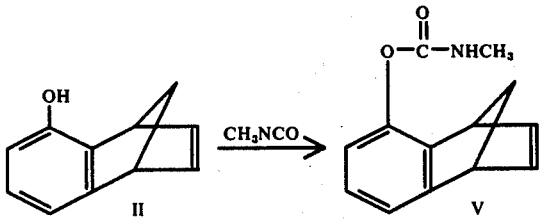

The phenol, II (1.2 g.) was dissolved in benzene (50 ml.) and placed in a pressure bottle. Methyl isocyanate (0.43 g.) was added followed by two drops of dibutyltin diacetate. The solution was then heated at 100° C. overnight. Removal of the solvent gave a light yellow solid (1.5 g.), which recrystallized from methyl ethyl ketone to give the carbamate V, (0.9 g.) m.p., 158°–162° C. The structure was confirmed by the infrared spectrum, (C=O at 5.8$\mu$ as expected from the product).

EXAMPLE 6

Preparation of 5,6,7,8-tetrahydro-5,8-methano-1-naphthyl-N-methylcarbamate.

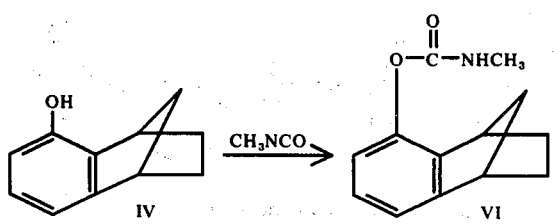

The phenol IV (1.3 g.) was dissolved in benzene (10 ml.), and methyl isocyanate (0.6 g.) and dibutyltin diacetate (two drops) added. The solution was allowed to stand at room temperature for 4 days, then petroleum ether was added to precipitate the carbamate VI, (1.6 g.), m.p. 160°–164° C.

EXAMPLE 7

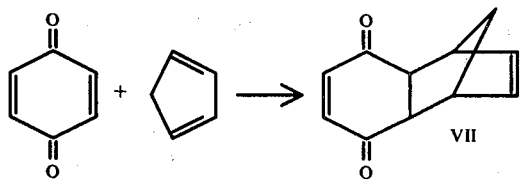

Benzoquinone-cyclopentadiene adduct (VII) was prepared by a non-catalytic Diels-Alder condensation of a benzene solution of cyclopentadiene with benzoquinone. The reaction mixture was stirred overnight at room temperature (slight initial exotherm) and the benzene was distilled off giving the adduct (VII) in quantitative yield. This procedure is reported in Beilstein.

EXAMPLE 8

4-methoxy-5,8-dihydro-5,8-methano-1-naphthol.

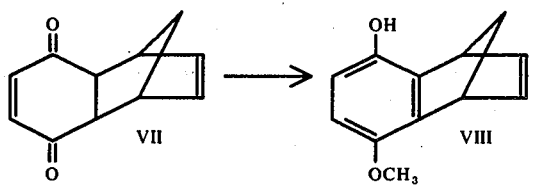

Adduct (VII) (34.8 g.) was added to a solution of 32 g. NaOH in 200 ml. water. The solution was stirred and 30.8 g. dimethyl sulfate added dropwise, giving a mild exotherm. Stirring was continued at room temperature for 3 hours. Then, the mixture was filtered, acidified with concentrated HCl, and extracted with chloroform. The organic layer was dried and evaporated to give a viscous brown oil. Distillation gave 6.1 g. of naphthol (VIII) as a thick yellow, viscous liquid, b. 178° C./0.1 mm.

EXAMPLE 9

4-Methoxy-5,8-dihydro-5,8-methano-1-naphthyl-N-methyl carbamate.

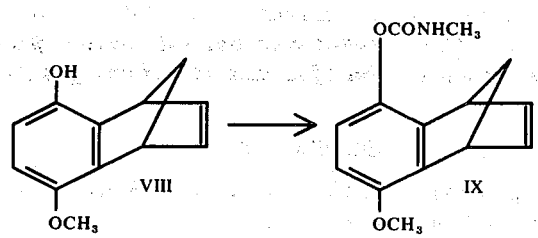

Naphthol (VIII) (5.0 g.) was dissolved in 50 ml. carbon tetrachloride, and 1.5 g. methyl isocyanate was added followed by two drops of dibutyltindiacetate catalyst. The solution was stirred overnight. The solvents were evaporated and the residue was recrystallized from methanol at −8° C. to give 3.4 g. of carbamate (IX) as a white solid, m.p. 104°–106° C.

EXAMPLE 10

4-Methoxy-5,6,7,8-tetrahydro-5,8-methano-1-naphthyl-N-methylcarbamate.

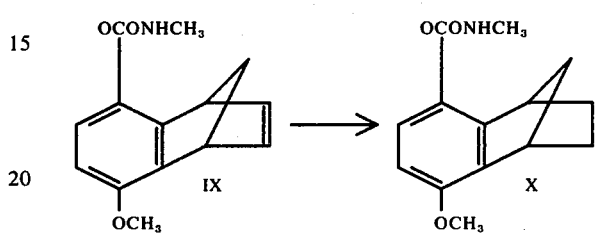

Carbamate (IX) (0.5 g.) was dissolved in 100 ml. methanol and 1 g. of catalyst (5% Pd on charcoal) was added. The mixture was shaken at room temperature in a small (Parr) bomb under 50 psi. hydrogen for 3 hours. Filtration and evaporation yield 0.5 g. of the carbamate (X).

EXAMPLE 11

4-Methoxy-5,8-dihydro-6,7-epoxy-5,8-methano-1-naphthyl-N-methylcarbamate.

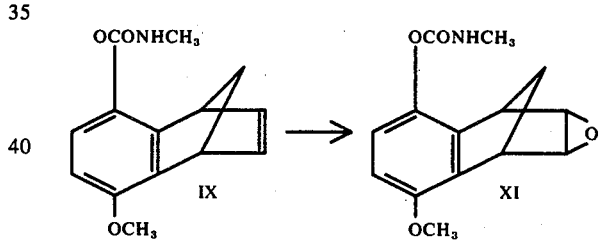

Carbamate (IX) (0.5 g.) was dissolved in 10 ml. chloroform m-Chloroperbenzoic acid (0.34 g.) in 10 ml. chloroform was added and the solution was allowed to stand overnight. The mixture was then filtered and washed with 5% aqueous sodium hydroxide and then water. The organic layer was dried and evaporated to give 0.5 g. of carbamate (XI).

EXAMPLE 12

The compound of Example 5 was subjected to the afore-described tests. The results are set forth in the Table.

EXAMPLE 13

The compound of Example 6 was subjected to the afore-described tests. The results are set forth in the Table.

EXAMPLE 14

The compound of Example 9 was subjected to the afore-described tests. The results are set forth in the Table.

EXAMPLE 15

The compound of Example 10 was subjected to the afore-described tests. The results are set forth in the Table.

EXAMPLE 16

The compound of Example 11 was subjected to the afore-described tests. The results are set forth in the Table.

TABLE

| Concn. P.P.M. | Bean Beatle | Southern Armyworm | Spider Mite | Housefly | Bean Aphid | Boll Weevil | Mosquito Larvae |
|---|---|---|---|---|---|---|---|
| EXAMPLE 12 | | | | | | | |
| 500 | 100 | 20 | 90 | 50 | 100 | 70 | 1/100 |
| 100 | 30 | — | 40 | — | 100 | — | 0.1/70 |
| 10 | 0 | — | 0 | — | 90 | — | 0.01/0 |
| EXAMPLE 13 | | | | | | | |
| 500 | 100 | 0 | 40 | 20 | 30 | 30 | 1/90 |
| 100 | 100 | — | — | — | — | — | 0.1/40 |
| 10 | 100 | — | — | — | — | — | 0.01/20 |
| EXAMPLE 14 | | | | | | | |
| 500 | 100 | 0 | 20 | 40 | 100 | 100 | — |
| 100 | 100 | — | — | — | 100 | 80 | — |
| 10 | 40 | — | — | — | 0 | 20 | — |
| EXAMPLE 15 | | | | | | | |
| 500 | 100 | 40 | 20 | 20 | 100 | 80 | — |
| 100 | 100 | — | — | — | 100 | 0 | — |
| 10 | 100 | — | — | — | 20 | 0 | — |
| EXAMPLE 16 | | | | | | | |
| 500 | 100 | 40 | 20 | 20 | 50 | 20 | — |
| 100 | 100 | — | — | — | — | — | — |
| 10 | 60 | — | — | — | — | — | — |

Although the present invention has been described with preferred embodiments, it is to be understood that modifications and variations may be resorted to, without departing from the spirit and scope of this invention, as those skilled in the art will readily understand. Such variations and modifications are considered to be within the purview and scope of the appended claims.

What is claimed is:

1. A method for combatting insects that comprises contacting them with an insecticidally effective amount of a carbamate having the formula:

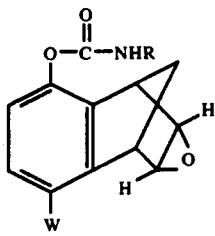

wherein R is alkyl ($C_1$-$C_5$) and W is hydrogen or alkoxy ($C_1$-$C_5$).

2. The method of claim 1, wherein said carbamate is 4-methoxy-5,8-dihydro-6,7-oxo-5,8-methano-N-methylcarbamate.

3. An insecticidal composition comprising a carrier and a carbamate having the formula:

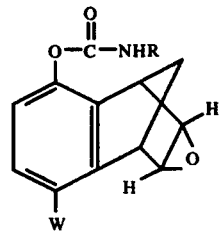

wherein R is alkyl ($C_1$-$C_5$) and W is hydrogen or alkoxy ($C_1$-$C_5$).

4. The composition of claim 3, wherein said carbamate is 4-methoxy-5,8-dihydro-6,7-oxo-5,8-methano-N-methylcarbamate.

5. A carbamate having the formula:

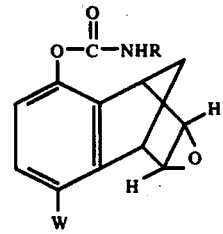

wherein R is alkyl ($C_1$-$C_5$) and W is hydrogen or alkoxy ($C_1$-$C_5$).

6. A compound of claim 5, wherein said compound is 4-methoxy-5,8-dihydro-6,7-epoxy-5,8-methano-1-naphthyl-N-methyl-carbamate.

* * * * *